(12) United States Patent
Fontanarosa et al.

(10) Patent No.: US 11,278,742 B2
(45) Date of Patent: Mar. 22, 2022

(54) IMAGE GUIDED TREATMENT DELIVERY

(71) Applicant: KONINKLIJKE PHILIPS N.V., Eindhoven (NL)

(72) Inventors: Davide Fontanarosa, Neerpelt (BE); Saskia Maria Camps, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 705 days.

(21) Appl. No.: 16/091,117

(22) PCT Filed: Apr. 24, 2017

(86) PCT No.: PCT/EP2017/059588
§ 371 (c)(1),
(2) Date: Oct. 4, 2018

(87) PCT Pub. No.: WO2017/186610
PCT Pub. Date: Nov. 2, 2017

(65) Prior Publication Data
US 2019/0117999 A1    Apr. 25, 2019

(30) Foreign Application Priority Data

Apr. 28, 2016 (EP) ..................................... 16167517
Jul. 14, 2016 (EP) ..................................... 16179436

(51) Int. Cl.
*A61N 5/10* (2006.01)
*A61B 8/08* (2006.01)
(Continued)

(52) U.S. Cl.
CPC ............ *A61N 5/1049* (2013.01); *A61B 8/085* (2013.01); *A61B 8/4218* (2013.01);
(Continued)

(58) Field of Classification Search
CPC .. A61N 5/1049; A61N 5/1058; A61N 5/1069; A61N 5/1038; A61N 5/103;
(Continued)

(56) References Cited

U.S. PATENT DOCUMENTS 6,961,405 B2   11/2005   Scherch
7,438,685 B2   10/2008   Burdette
(Continued)

FOREIGN PATENT DOCUMENTS

CN       202458460 U      10/2012
WO    WO-2004033041 A1 *  4/2004    ........... A61B 8/4245

OTHER PUBLICATIONS

Lattanzi, J. et al., "A comparison of daily CT localization to a daily ultrasound based system in prostate cancer," IJROBP, 43 (4), pp. 719-725, 1999.
(Continued)

*Primary Examiner* — Carolyn A Pehlke
(74) *Attorney, Agent, or Firm* — Sherry Austin

(57) ABSTRACT

The invention relates to a system (1) for image based guidance of treatment delivery to a patient. The system is adapted to determine spatial parameters defining a position and orientation of an ultrasound probe (8) on the basis of a reference image which has been used for preparing a treatment plan. This can provide a certain degree of automation in arranging the ultrasound probe, in order to decrease user dependence and improve the usability for relatively untrained operators. Moreover, since the reference image is also used for generating the treatment plan, i.e. since the same image is used for generating the treatment plan and for determining the position and orientation of the ultrasound probe, it is not necessarily required to acquire an additional image. This can allow for a reduced radiation dose applied to the parts of the patient not being the target to be treated.

10 Claims, 10 Drawing Sheets

(51) Int. Cl.
*A61B 8/00* (2006.01)
*A61B 90/00* (2016.01)
*A61B 34/20* (2016.01)
*A61B 34/10* (2016.01)

(52) U.S. Cl.
CPC .......... *A61B 8/4245* (2013.01); *A61B 8/5223* (2013.01); *A61B 8/5238* (2013.01); *A61N 5/107* (2013.01); *A61N 5/1038* (2013.01); *A61N 5/1039* (2013.01); *A61N 5/1067* (2013.01); *A61N 5/1069* (2013.01); *A61B 8/5261* (2013.01); *A61B 2034/107* (2016.02); *A61B 2034/2063* (2016.02); *A61B 2090/364* (2016.02); *A61B 2090/378* (2016.02); *A61N 2005/1058* (2013.01)

(58) Field of Classification Search
CPC ............ A61N 2005/1058; A61B 8/085; A61B 8/4218; A61B 8/4245
See application file for complete search history.

(56) References Cited

U.S. PATENT DOCUMENTS

| | | | |
|---|---|---|---|
| 9,108,048 | B2 | 8/2015 | Maurer et al. |
| 9,320,916 | B2 | 4/2016 | Sumanaweera |
| 9,572,545 | B2 | 2/2017 | Chen et al. |
| 2005/0182316 | A1 | 8/2005 | Burdette et al. |
| 2006/0241443 | A1 | 10/2006 | Whitmore et al. |
| 2008/0161687 | A1 | 7/2008 | Suri |
| 2009/0024030 | A1 | 1/2009 | Lachaine et al. |
| 2012/0035462 | A1 | 2/2012 | Maurer et al. |
| 2012/0296213 | A1 | 11/2012 | Mauldin et al. |
| 2014/0039314 | A1 | 2/2014 | Stoianovici et al. |
| 2015/0209599 | A1* | 7/2015 | Schlosser ............. A61B 6/4417 600/427 |
| 2016/0000409 | A1 | 1/2016 | Bruder et al. |
| 2016/0143620 | A1* | 5/2016 | Ohta .................... A61B 8/4218 600/440 |
| 2016/0242745 | A1* | 8/2016 | Yang .................... A61B 5/055 |
| 2020/0268071 | A1 | 8/2020 | Newcomb et al. |

OTHER PUBLICATIONS

Fontanarosa, D. at al., "Review of ultrasound image guidance in external beam radiotherapy: I. Treatment planning and inter-fraction motion management." Phys Med Biol. 2015;60(3):R77-R114. doi:10.1088/0031-9155/60/3/R77.

Langen, K.M. et al., "Evaluation of ultrasound-based prostate localization for image-guided radiotherapy." Int J Radiat Oncol Biol Phys. 2003;57(3):635-644. doi:10.1016/S0360-3016(03)00633-3.

Van Der Meer, S. at al., "Critical assessment of intramodality 3D ultrasound imaging for prostate IGRT compared to fiducial markers." Med Phys. 2013;40(2013):071707-1-071707-071711. doi: 10.1118/1.4808359.

Camps, S.M. et al., "Geometry based transperineal ultrasound probe positioning for image guided radiotherapy". American Association of Physicist in Medicine Conference, Jul. 21, 2016, Conference Paper.

* cited by examiner

IMAGE GUIDED TREATMENT DELIVERY

CROSS-REFERENCE TO PRIOR APPLICATIONS

This application is the U.S. National Phase application under 35 U.S.C. § 371 of International Application Serial No. PCT/EP2017/059588, filed on Apr. 24, 2017, which claims the benefit of European Patent Application No. 16167517.8 and 16179436.7, filed on Apr. 28, 2016 and Jul. 14, 2016. This application is hereby incorporated by reference herein.

FIELD OF THE INVENTION

The invention relates to a system and computer program for image based guidance of treatment delivery to a patient. Moreover, the invention relates to a method for assisting in providing an image.

BACKGROUND OF THE INVENTION

US 2006/0241443 A1 discloses a system of targeting therapy such as radiation treatment to a patient. The system is adapted to identify a target lesion inside the patient by using a first image obtained from an imaging modality like a computed tomography imaging system. The system is further adapted to provide a static ultrasound image and to identify an anatomical feature inside the patient on the static ultrasound image. Moreover, the system is adapted to register the first image with the static ultrasound image and to track a movement of the anatomical feature during respiration in real time using ultrasound so that therapy delivery to the target lesion is triggered based on the movement of the anatomical feature and the registered images.

US 2005/0182316 A1 discloses a system for localizing a medical imaging probe. An image of a reference target is generated with a camera that is attached to the medical imaging probe, wherein the reference target is remote from the probe and located in a room at a known position relative to a coordinate system. The position of the medical imaging probe is determined relative to the coordinate system at least partly on the basis of the generated image of the reference target.

US 2012/0035462 A1 discloses a system for tracking an anatomy of interest. The system comprises an ultrasound probe configured to obtain ultrasound images of the anatomy of interest, a non-ultrasound imaging modality configured to obtain an image of the anatomy of interest, and a controller in operable communication with the ultrasound probe and the non-ultrasound imaging modality, wherein the controller comprises a processor and a computer-readable medium. The computer-readable medium stores a pre-acquired three-dimensional image of the anatomy of interest in a first reference frame and instructions for causing the processor to perform following functions: a) instructing the non-ultrasound imaging modality to obtain a non-ultrasound image of the anatomy of interest in a second reference frame, b) instructing the ultrasound probe to obtain a set-up ultrasound image of the anatomy of interest substantially simultaneously as the non-ultrasound image is obtained, c) establishing a transformation between the first and second reference frames by registering the pre-acquired three-dimensional image and the non-ultrasound image, d) instructing the ultrasound probe to obtain an intrafraction ultrasound image of the anatomy of interest, e) registering the intrafraction ultrasound image with the set-up ultrasound image, and f) tracking the anatomy of interest motion based on the registered intrafraction ultrasound image.

US 2014/0039314 A1 discloses a system for providing navigation during surgery. The system comprises a robotic apparatus for manipulating an ultrasound imaging transducer in tandem with a medical instrument suitable as a fiducial marker. A region of interest is scanned and a parameter of an anatomical feature therein is measured by using the ultrasound imaging transducer. A position of the ultrasound imaging transducer is tracked during surgery using a programmable computer link to the robotic apparatus, wherein this tracking leads to tracking information. The tracking information is applied to construct a three-dimensional model of the region of interest in which the medical instrument can be visualized during the surgery, wherein the medical instrument is manipulated about the region of interest by using information derived from the three-dimensional model.

US 2016/0000409 A1 discloses a system for estimating ultrasound image quality at a variety of positions to determine a desired ultrasound transducer position. The system comprises an input module configured to receive anatomical image data from a first imaging modality, wherein the anatomical image data include a target. The system further comprises an image quality estimation module coupled with the input module, wherein the image quality estimation module is configured to estimate ultrasound image quality when imaging the target at a position relative to the target by analyzing the anatomical image data to estimate ultrasound velocity along a route from the position to the target, wherein the route passes through one or more tissue types. Moreover, the system comprises a display module coupled with the image quality estimation module, wherein the display module is configured to output an indication of the ultrasound image quality at positions relative to the target.

It is known to use, for instance, a radiotherapy system for treatment delivery to a patient. A radiotherapy system can comprise a radiation source for treating a target by using ionizing radiation and an x-ray imaging system like a computed tomography imaging system for generating an image of the patient, wherein this image is used for determining the position, the orientation and dimensions of the target within the patient immediately before the radiotherapy is carried out. This spatial information can be used to, for instance, arrange the patient correctly or to adapt a given treatment plan such that the target is accurately met by the ionizing radiation.

This determination of the position, orientation and dimensions of the target within the patient by using x-rays leads to a relatively high radiation dose applied to parts of the patient not being the actual target, whereas ideally only the target should receive a high radiation dose.

SUMMARY OF THE INVENTION

It is an object of the present invention to provide a system and computer program for image based guidance of treatment delivery to a patient, which allow for a reduced radiation dose applied to parts of the patient not being the target. It is a further object of the present invention to provide a method for assisting in providing an image.

In a first aspect of the present invention a system for image based guidance of treatment delivery to a patient is presented, wherein the system comprises:

a reference image providing unit for providing a reference image of a patient, wherein the reference image shows a target to be treated and an organ at risk within the patient, a treatment plan providing unit for providing a treatment plan for the treatment delivery, which plan has been prepared on the basis of the reference image, a spatial parameters determining unit for determining spatial parameters defining a position and orientation of an ultrasound probe, which is adapted to be used for generating an ultrasound image of the patient, on the basis of the reference image, wherein the system further comprises a field of view providing unit for providing a field of view of the ultrasound probe and wherein the spatial parameters determining unit is adapted to determine a position, an orientation and dimensions of the target within the reference image, to determine a position, an orientation and dimensions of the organ at risk within the reference image, and to determine the spatial parameters based on the determined positions, orientations and dimensions of the target and the organ at risk in the reference image and the provided field of view such that the target and the organ at risk are within the field of view.

Since the spatial parameters determining unit is adapted to determine the spatial parameters defining the position and orientation of the ultrasound probe on the basis of the reference image, the arrangement of the ultrasound probe can be automatically determined, wherein this automatically determined arrangement of the ultrasound probe can be used for generating an ultrasound image for image based guidance of treatment delivery. Thus, the spatial parameters defining the position and orientation of the ultrasound probe can be automatically determined and then the ultrasound probe can be arranged in accordance with the automatically determined spatial parameters. This automation decreases user dependence and improves the usability for relatively untrained operators. In this way the use of ultrasound in the treatment delivery workflow will be appealing for hospitals and so the patients can fully benefit from the unique characteristics of this imaging modality. In the end this can result in better outcomes for the patients, while reducing toxicity and improving quality of life at the same time. In particular, the use of ultrasound will reduce the radiation dose applied to parts of the patient not being a target of the actual treatment delivery. Moreover, since the reference image is also used for generating the treatment plan, i.e. since the same image is used for generating the treatment plan and for determining the position and orientation of the ultrasound probe, the radiation dose applied to the parts of the patient not being the target can be further reduced.

The treatment plan providing unit can be a storing unit in which the treatment plan is stored already and from which the treatment plan can be retrieved for providing the same. However, the treatment plan providing unit can also be a receiving unit, i.e. a plan input, for receiving the treatment plan from a treatment plan generating unit, or the treatment plan providing unit can be the treatment plan generating unit itself.

The reference image shows the target to be treated within the patient, wherein the system comprises the field of view providing unit for providing the field of view of the ultrasound probe and wherein the spatial parameters determining unit is adapted to determine a position, an orientation and dimensions of the target within the reference image and to determine the spatial parameters based on the determined position, orientation and dimensions of the target in the reference image and the provided field of view such that the target is within the field of view. This allows for a determination of the spatial parameters such that the ultrasound image really shows at least the target with relatively low computational efforts.

Moreover, the reference image also shows the organ at risk within the patient, wherein the spatial parameters determining unit is adapted to determine also a position, an orientation and dimensions of the organ at risk within the reference image and to determine the spatial parameters based on the determined positions, orientations and dimensions of the target and the organ at risk in the reference image and the provided field of view such that the target and the organ at risk are within the field of view. This allows for a determination of the spatial parameters such that the ultrasound image really shows not only the target, but also at least a part of the organ at risk, with relatively low computational efforts.

It is preferred that the system further comprises an imaging part indication providing unit for providing an imaging part indication defining a mandatory part of the organ at risk to be mandatorily ultrasonically imaged, wherein the spatial parameters determining unit is adapted to determine the spatial parameters also based on the provided imaging part indication. The spatial parameters determining unit is preferentially adapted to determine the spatial parameters defining the position and orientation of the ultrasound probe such that the indicated mandatorily part is within the field of view of the ultrasound probe. The imaging part indication providing unit can be adapted to provide the imaging part indication such that it also defines an optional part of the organ at risk to be optionally ultrasonically imaged. The spatial parameters determining unit can be adapted to determine the spatial parameters defining the position and orientation of the ultrasound probe based on the provided imaging part indication such that the mandatory part is surely within the field of view of the ultrasound probe and from the optional part as much as possible is within the field of view of the ultrasound probe.

Preferentially, the reference image also shows an ultrasound blocking structure, wherein the spatial parameters determining unit is adapted to also determine a position, an orientation and dimensions of the ultrasound blocking structure within the reference image, wherein the spatial parameters determining unit is adapted to determine the spatial parameters also based on the determined position, orientation and dimensions of the ultrasound blocking structure. In particular, the spatial parameters determining unit is adapted to determine the spatial parameters such that there is no ultrasound blocking structure between a) the ultrasound probe and b) the target and, if it is defined, the organ at risk to be ultrasonically image. By also considering the ultrasound blocking structure the likelihood that the target and the organ at risk are not visible in the ultrasound image due to an ultrasound blocking structure can be significantly reduced.

In an embodiment the spatial parameters determining unit is adapted to determine, without considering the position, orientation and dimensions of the ultrasound blocking structure, several sets of spatial parameters defining several possible positions and orientations of the ultrasound probe such that in each position and orientation at least the target and optionally also an organ at risk is within the provided field of view and to select, by considering the position of the ultrasound blocking structure, at least one of these sets of spatial parameters which defines a possible position and orientation, at which the ultrasound blocking structure is not in between a) the ultrasound probe and b) at least the target and optionally the organ at risk to be ultrasonically imaged. This allows determining the spatial parameters of the ultrasound probe such that the target and optionally also an organ at risk are surely shown in the ultrasound image with relatively low computational efforts.

The spatial parameters determining unit can be adapted to segment the target and optionally also an organ at risk in the ultrasound image for determining the respective position, orientation and dimensions within the ultrasound image or, in other words, the respective region of the ultrasound image occupied by the target or the organ at risk, respectively. Known segmentation algorithms can be used for performing these segmentations.

In an embodiment the system further comprises an ultrasound image providing unit for providing an ultrasound image generated by using the ultrasound probe in the position and orientation defined by the determined spatial parameters, wherein the treatment plan providing unit is arranged to adapt the treatment plan on the basis of a comparison of the reference image and the ultrasound image. Moreover, the system can comprise a patient support and a controller for controlling the patient support on the basis of a comparison of the reference image and the ultrasound image. The adaptation of the treatment plan and the control of the patient support depending on a comparison of the reference image and the ultrasound image can improve the accuracy of delivering the treatment to the target.

Preferentially, the system further comprises a holding mechanism for holding the ultrasound probe in accordance with the determined spatial parameters such that the ultrasound probe assumes the position and orientation defined by the determined spatial parameters. In particular, the holding mechanism comprises a holder for holding the ultrasound probe and a support structure to which the holder is attached, wherein the position and orientation of the support structure is modifiable by modifying positions and/or orientations of movable elements of the support structure, which are defined by movable element parameters, wherein the spatial parameters determining unit is adapted to determine, as the spatial parameters defining the position and orientation of the ultrasound probe, the movable element parameters. The system can further comprise an energy source for providing energy to be applied to the target in accordance with the treatment plan.

In another aspect of the present invention a method for assisting in providing an image is presented, wherein the method comprises:

providing a reference image of a patient, wherein the reference image shows a target to be treated and an organ at risk within the patient, providing a treatment plan for the treatment delivery, which plan has been prepared on the basis of the reference image, determining spatial parameters defining a position and orientation of an ultrasound probe, which is adapted to be used for generating an ultrasound image, on the basis of the reference image, wherein a field of view of the ultrasound probe is provided, wherein a position, an orientation and dimensions of the target within the reference image are determined, wherein a position, an orientation and dimensions of the organ at risk within the reference image are determined, and wherein the spatial parameters are determined based on the determined positions, orientations and dimensions of the target and the organ at risk in the reference image and the provided field of view such that the target and the organ at risk are within the field of view.

Moreover, in an aspect of the present invention a computer program for image based guidance of treatment delivery to a patient is presented, the computer program comprising program code means for causing a system as defined in claim 1 to carry out the following steps, when the computer program is run on the system:

providing a reference image of a patient, wherein the reference image shows a target to be treated and an organ at risk within the patient, providing a treatment plan for the treatment delivery, which plan has been prepared on the basis of the reference image, determining spatial parameters defining a position and orientation of an ultrasound probe, which is adapted to be used for generating an ultrasound image, on the basis of the reference image, wherein a field of view of the ultrasound probe is provided, wherein a position, an orientation and dimensions of the target within the reference image are determined, wherein a position, an orientation and dimensions of the organ at risk within the reference image are determined, and wherein the spatial parameters are determined based on the determined positions, orientations and dimensions of the target and the organ at risk in the reference image and the provided field of view such that the target and the organ at risk are within the field of view.

It shall be understood that the system of claim 1, the method of claim 11 and the computer program of claim 12 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
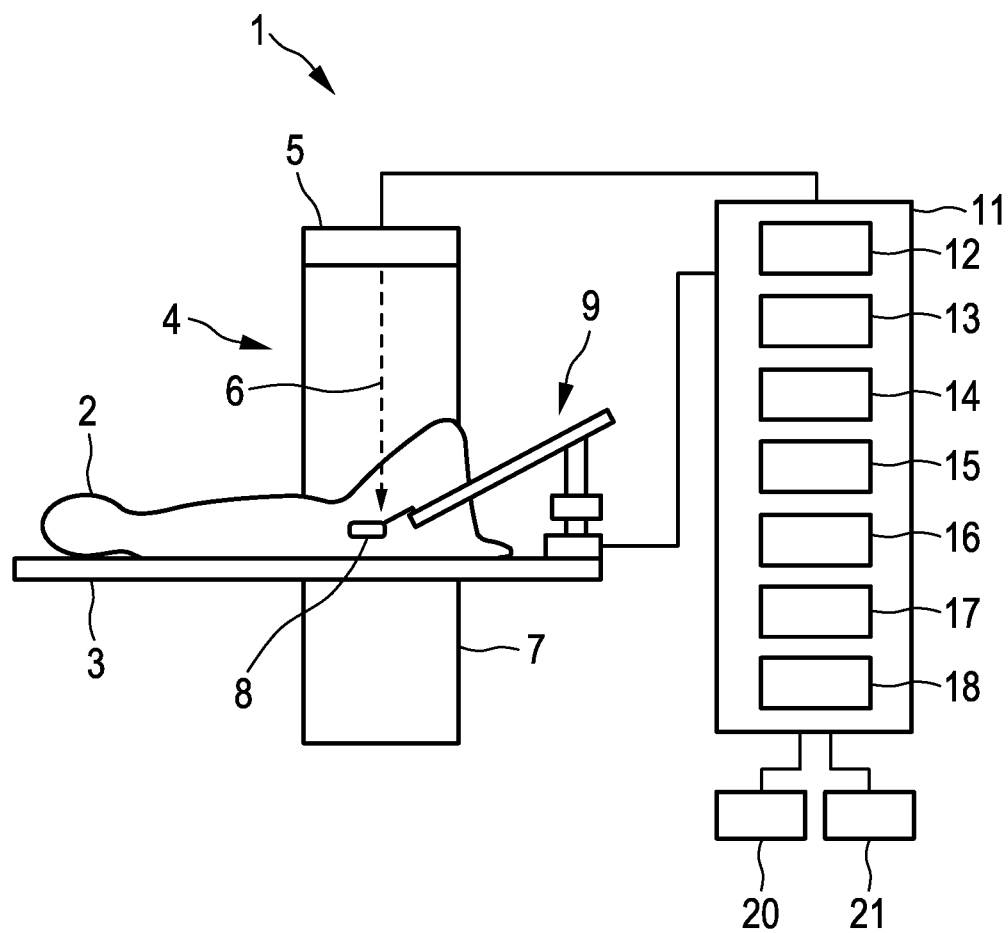
FIG. 1 shows schematically and exemplarily an embodiment of a system for image based guidance of treatment delivery to a patient.

FIG. 1 shows schematically and exemplarily an embodiment of a system 1 for image based guidance of treatment delivery to a patient 2. The patient 2 is lying on a patient support 3 like a patient table. The system 1 comprises a radiation device 4 with an energy source 5 for providing energy 6 to be applied to a target within the patient 2. In this embodiment the energy source 5 is a radiation source emitting ionizing radiation like x-rays, gamma rays, et cetera. The radiation device 4 further comprises a rotatable gantry 7, wherein to one end of the rotatable gantry 7 the radiation source 5 is attached, in order to allow for a rotation of the radiation source 5 around the patient 2, i.e. in order to allow for an emission of the ionizing radiation 6 in different emission directions relative to the patient 2. The system 1 further comprises a controlling and processing device 11 with a treatment plan providing unit 12 for providing a treatment plan. The treatment plan providing unit 12 can be a storing unit for storing an already prepared treatment plan and for providing this stored treatment plan. However, the treatment plan providing unit 12 can also be a receiving unit for receiving a treatment plan from, for instance, a treatment plan generating unit. The treatment plan providing unit 12 can also be the treatment plan generating unit itself. The treatment plan is generated based on a planning image showing the interior of the patient 2, especially the target, organs at risk and ultrasound blocking structures like bones, wherein known treatment planning algorithms might be used.

In this embodiment the planning image is a computed tomography image which has been generated by using a computed tomography imaging system. In another embodiment the planning image can be generated by using another imaging modality like a magnetic resonance imaging system. The computed tomography image has been generated by a computed tomography imaging system being separate from the radiation device 4, wherein the computed tomography image is registered with the radiation device 4 by using known registration techniques. In other embodiments it is also possible that the computed tomography imaging system is integrated with the radiation device 4 such that the computed tomography image is registered with the radiation device 4 from the beginning and it is not necessary to apply the registration techniques.

The system 1 further comprises an ultrasound probe 8 to be used for generating an ultrasound image of the interior of the patient 2 and an ultrasound image providing unit 15 for providing the ultrasound image generated by using the ultrasound probe 8. The system 1 can therefore also be regarded as being a system for ultrasound based guidance of treatment delivery of a patient. In this embodiment the ultrasound image providing unit 15 is adapted to control the ultrasound probe 8 such that it transmits and receives ultrasound signals and provides the received ultrasound signals to the ultrasound image providing unit 15 for allowing the ultrasound image providing unit 15 to generate the ultrasound image based on the received ultrasound signals.

Figure 2:
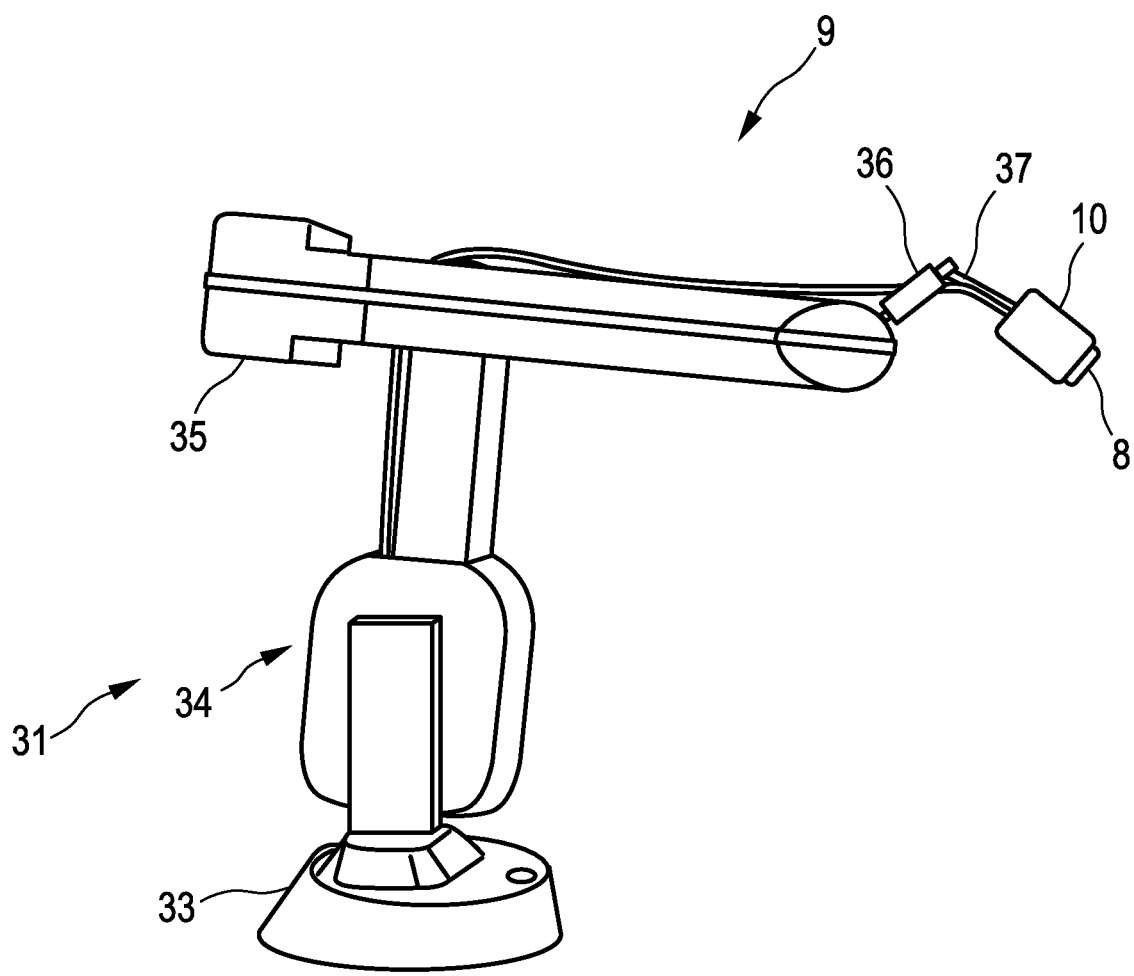
FIG. 2 shows schematically and exemplarily a holding mechanism for holding an ultrasound probe.

The system 1 further comprises a holding mechanism 9 schematically and exemplarily shown in more detail in FIG. 2. The holding mechanism 9 comprises a holder 10 for holding the ultrasound probe 8. The holder 10 is attached to a support structure 31, wherein the position and orientation of the support structure 31, i.e. the position and orientation of movable elements 33 . . . 37 of the support structure 31 relative to each other, is modifiable, in order to allow for different positions and orientations of the ultrasound probe 8 relative to the patient 2. The support structure 31 can be regarded as being a mechanical or robotic arm. The position and orientation of the support structure 31 is defined by movable element parameters defining the position and orientation of each movable element 33 . . . 37 and hence of the entire support structure 31.

The system 1 further comprises a reference image providing unit 13 for providing a reference image of the interior of the patient 2. The reference image providing unit 13 is adapted to provide the planning image as the reference image. Thus, for providing the reference image it is not necessary to acquire an additional image, but the already present planning image can be used. The reference image providing unit 13 can be a storing unit in which the reference image is stored already, wherein the reference image providing unit 13 can be adapted to provide the stored reference image, or the reference image providing unit can be a receiving unit for receiving the reference image from, for instance, an imaging system like a computed tomography imaging system or from the treatment plan providing unit 12, if the treatment plan providing unit 12 has stored the reference image which is also used for generating the treatment plan. The reference image shows the target, the organs at risk, the ultrasound blocking structures and possibly further structures.

The system 1 further comprises an imaging part indication providing unit 14 for providing an imaging part indication defining parts of the organs at risk to be mandatorily ultrasonically imaged and parts of the organs at risk to be optionally ultrasonically imaged. Moreover, the system 1 comprises a field of view providing unit 16 for providing a field of view of the ultrasound probe 8 and a spatial parameters determining unit 17 for determining the positions, orientations and dimensions of the target, the organs at risk and the ultrasound blocking structures within the reference image and for determining spatial parameters defining a position and orientation of the ultrasound probe 8 based on the determined positions, orientations and dimensions of the target, the organs at risk and the blocking structures, the provided field of view of the ultrasound probe 8 and the provided imaging part indication such that the target and the mandatory parts of the organs at risk are within the provided field of view of the ultrasound probe, as much as possible of the optional parts of the organs at risk are also within the provided field of view of the ultrasound probe and the ultrasound blocking structures are not arranged in between the ultrasound probe 8 and the target and the organs at risk to be imaged.

Figure 3:
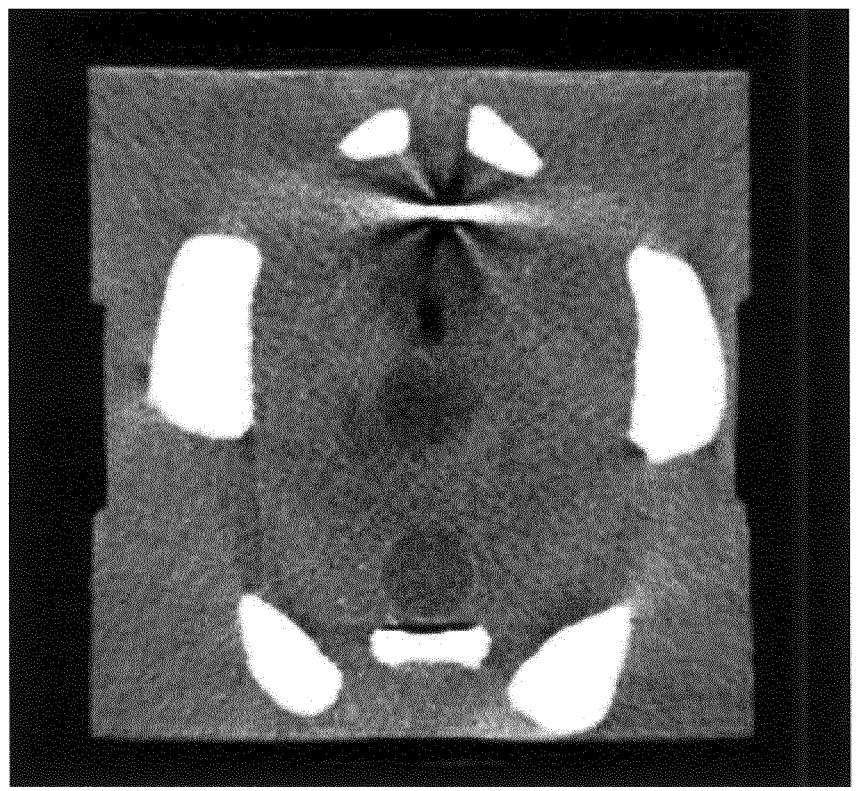
FIG. 3 shows schematically and exemplarily a reference image.
Figure 4:
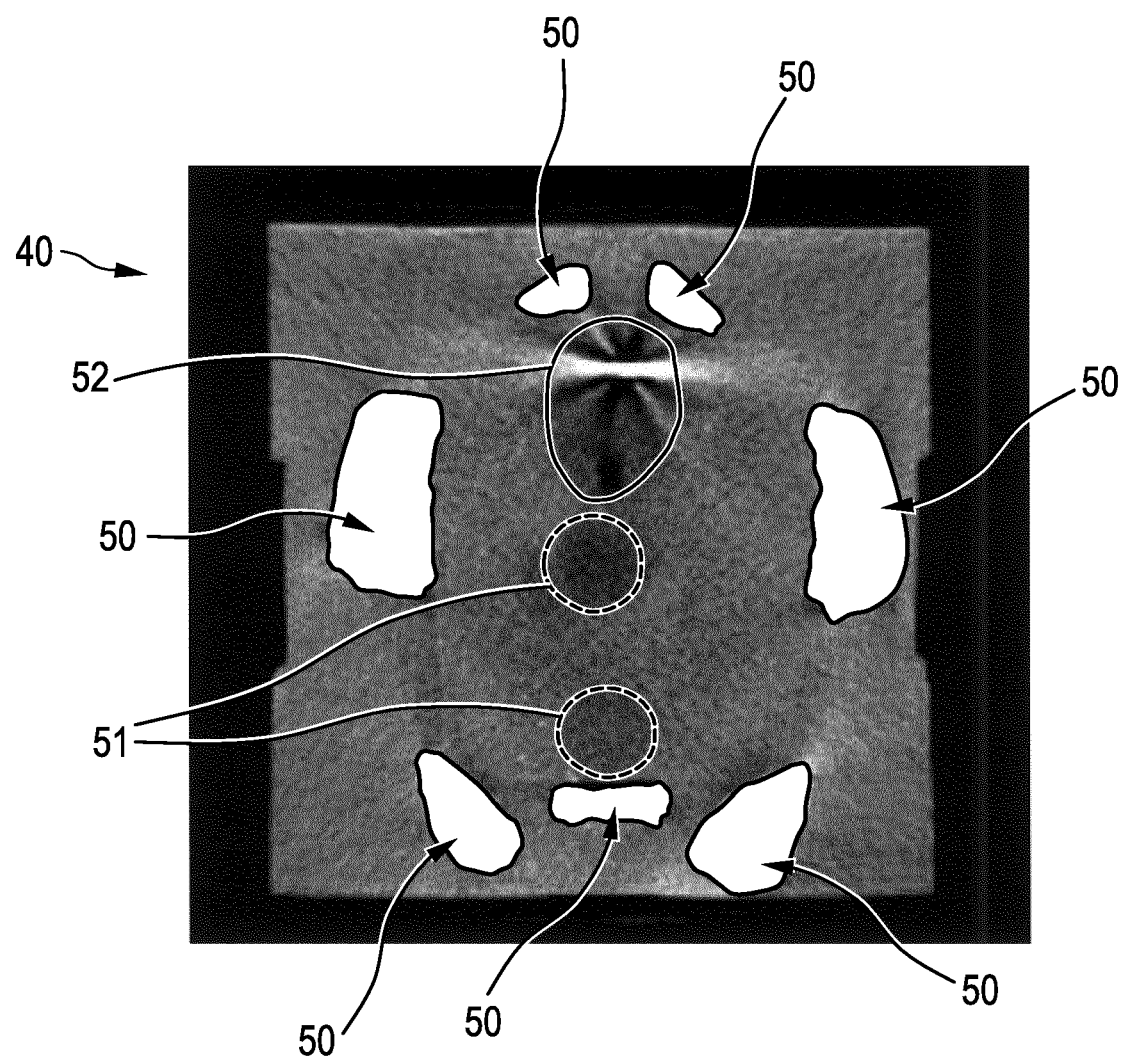
FIG. 4 shows schematically and exemplarily a target, organs at risk and ultrasound blocking structures segmented within the reference image.

FIG. 3 shows an example of a reference image 40 being a computed tomography image and being also used as the planning image. The spatial parameters determining unit 17 is adapted to determine the positions, orientations and dimensions of the target, the organs at risk and the ultrasound blocking structures by segmenting these elements in the provided reference image 40. For performing this segmentation known fully automatic or semi-automatic segmentation algorithms can be used. It is also possible that a graphical user interface is provided for allowing a user like a physician to completely manually segment the relevant structures. FIG. 4 exemplary shows the positions, orientations and dimensions of the target 52, the organs at risk 51 and the ultrasound blocking structures 50 as obtained by applying a fully automatic segmentation algorithm within the reference image 40. In this example the target 52 is the prostate, the organs at risk 51 are the bladder and the rectum and the ultrasound blocking structures 50 are the bones.

Figure 5:
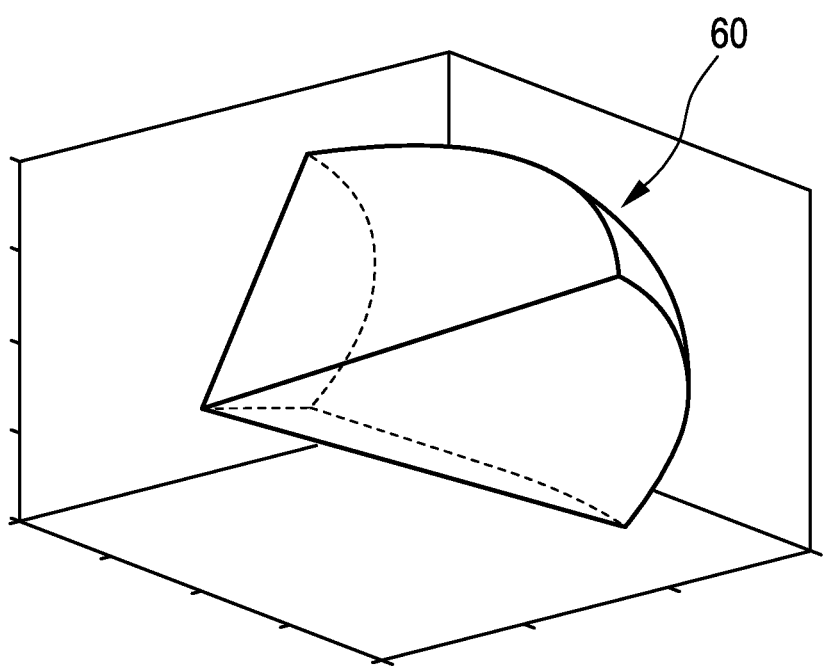
FIG. 5 shows schematically and exemplarily a field of view of the ultrasound probe.
Figure 6:
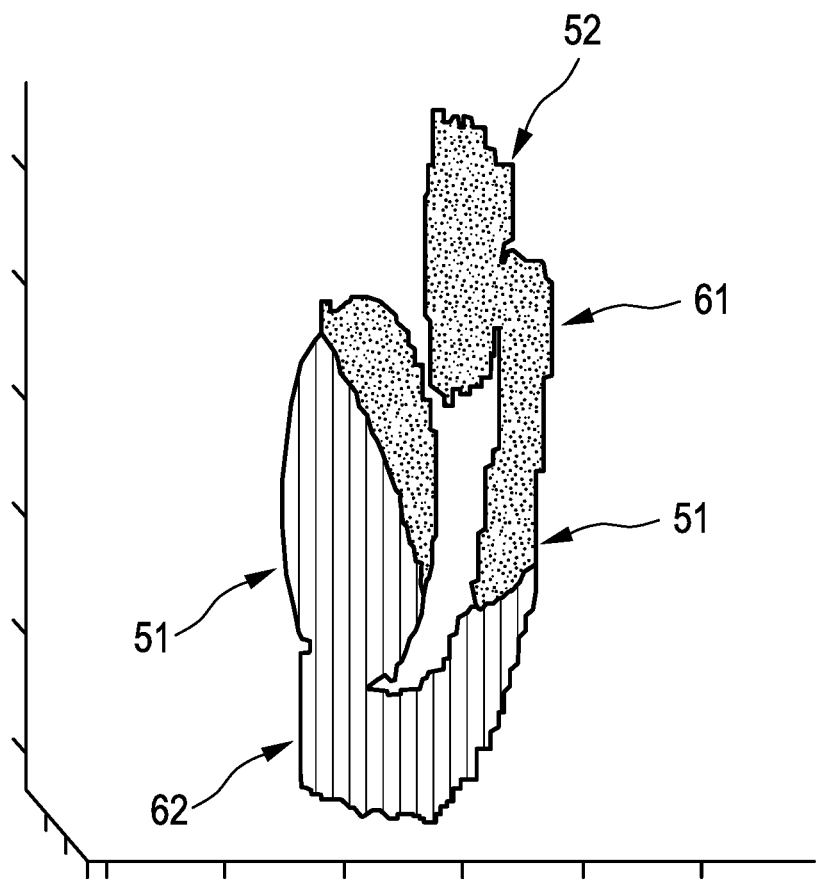
FIG. 6 illustrates schematically and exemplarily the target and parts of the organs at risk to be mandatorily imaged and further parts of the organs at risk to be optionally imaged.

The reference image 40 is a three-dimensional computed tomography image and the provided field of view 60 of the ultrasound probe 8, which is exemplarily illustrated in FIG. 5, is also three-dimensional. FIG. 6 schematically and exemplarily illustrates imaging part indications 61, 62 indicating which parts of the organs at risk 51 need to be mandatorily ultrasonically imaged (indicated by reference number 61) and which parts of the organs at risk 51 should be optionally imaged (indicated by reference number 62). These imaging part indications can be stored in the imaging part indication providing unit 14, wherein the imaging part indication providing unit 14 can be adapted to provide these already stored imaging part indications. However, the imaging part indication providing unit 14 can also be adapted to provide a graphical user interface allowing a user like a physician to manually indicate the mandatory and optional parts, wherein the imaging part indication providing unit 14 can be adapted to store these manually generated imaging part indications and to provide these stored imaging part indications to the spatial parameters determining unit 17. The user can use the graphical user interface via an input unit 20 like a keyboard, a computer mouse or a touch pad and an output unit 21 like a display.

Figure 7:
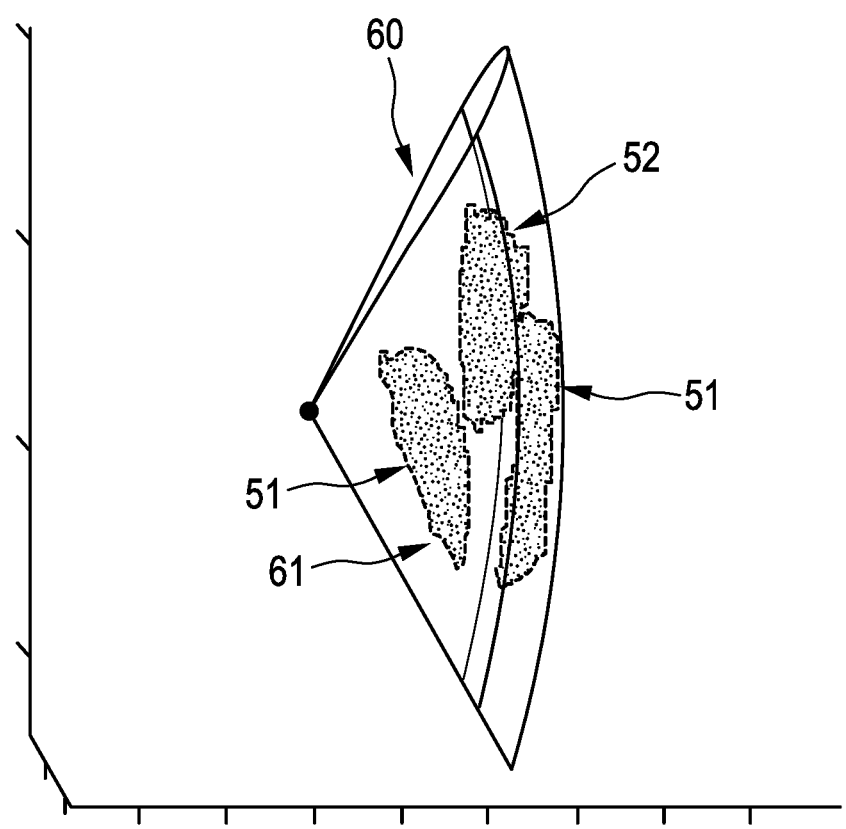
FIG. 7 shows schematically and exemplarily the target and the parts of the organs at risk to be mandatorily imaged within the field of view of the ultrasound probe.

The spatial parameters determining unit 17 can be adapted to determine the position of the centroid of the target and of the mandatory parts of the organs at risk to be imaged and to align the provided field of view with this determined centroid position. For instance, the field of view can be aligned such that the central line of the field of view traverses the centroid. The spatial parameters determining unit 17 can be further adapted to, if the field of view does not completely cover the target and the mandatory parts of the organs at risk, translate the field of view along one or several directions and/or rotate the field of view along one or several axes, until the target and the mandatory parts of the organs at risk are completely covered by the field of view. Preferentially, these steps are carried out several times, in order to determine several possible positions and orientations of the field of view, in which the field of view completely covers the target and the mandatory parts of the organs at risk. A solution showing the target and the mandatory parts of the organs at risk within the field of view 60 is schematically and exemplary illustrated in FIG. 7.

Figure 8:
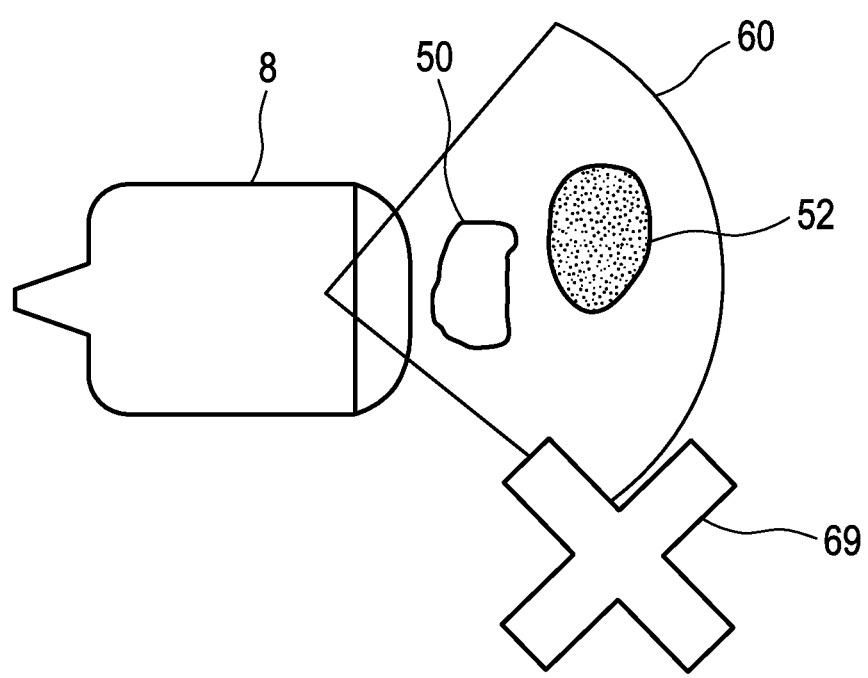
FIG. 8 illustrates schematically and exemplarily an unwanted position and orientation of the ultrasound probe at which an ultrasound blocking structure is in between the ultrasound probe and the target.

The spatial parameters determining unit 17 is adapted to determine the spatial parameters such that an ultrasound blocking structure 50 is not in between a) the ultrasound probe 8 and b) the target and the mandatory parts of the organs at risk to be imaged as schematically and exemplary illustrated in FIG. 8, wherein in FIG. 8 the cross 69 just indicates that the spatial parameters determining unit 17 is adapted to make sure that the spatial parameters are determined such that they do not define a positional arrangement as illustrated in FIG. 8. This determination of the spatial parameters such that an ultrasound blocking structure is not in between a) the ultrasound probe and b) the target and the mandatory parts of the organs at risk is preferentially performed by selecting from the several possible positions and orientations of the field of view, in which the field of view covers the target and the mandatory parts of the organs at risk, the possible positions and orientations in which the ultrasound blocking structures are not arranged in between a) the ultrasound probe and b) the target and the mandatory parts of the organs at risk.

Figure 9:
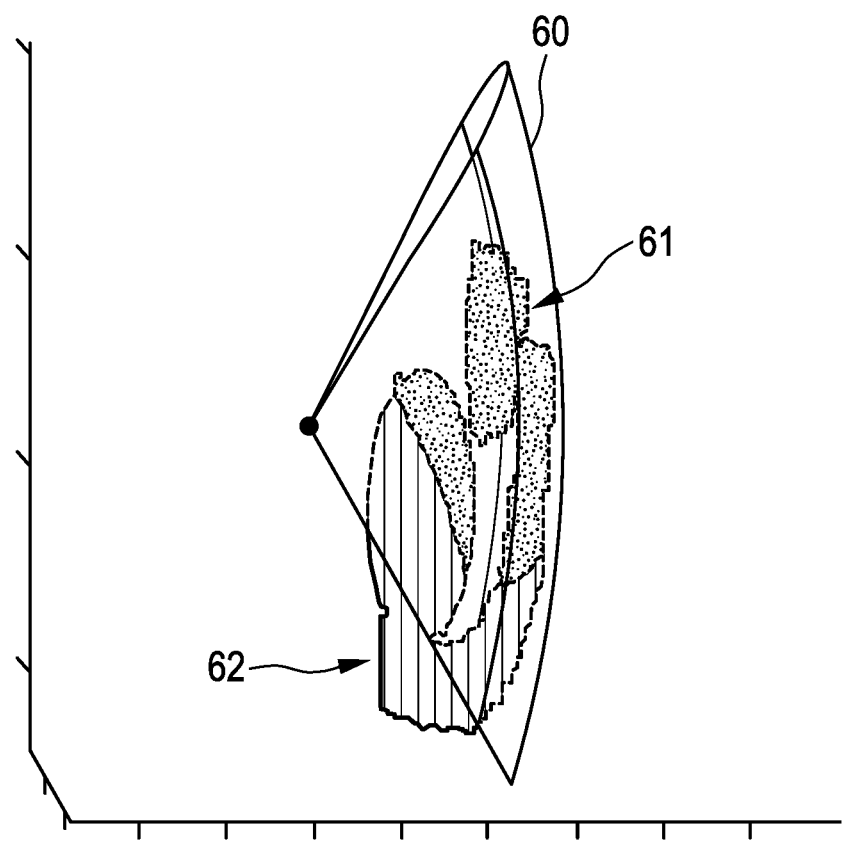
FIG. 9 illustrates schematically and exemplarily the target, parts of the organs at risk to be mandatorily imaged and also parts of the organs at risk to be optionally imaged within the field of view of the ultrasound probe.

The spatial parameters determining unit 17 is further adapted to determine the spatial parameters such that not only the target and mandatory parts of the organs at risk are within the field of view, but that also as much as possible of the optional parts of the organs at risk are within the field of view. FIG. 9 exemplarily shows a solution, wherein not only the target and the mandatory parts 61 are within the field of view 60, but also as much as possible of the optional parts 62. For instance, after the selection of the determined positions and orientations of the field of view such that the ultrasound blocking structures are not arranged in between a) the ultrasound probe and b) the target and the mandatory parts of the organs at risk, the field of view can again be translated along one or several directions and/or rotated along one or several axes, until also as much as possible of the optional parts of the organs at risk are within the field of view, wherein no ultrasound blocking structures should be arranged in between a) the ultrasound probe and b) the target, the mandatory parts of the organs at risk and the optional parts of the organs at risk.

The spatial parameters determining unit 17 is adapted to determine, as the spatial parameters defining the position and orientation of the ultrasound probe 8, the movable element parameters defining the positions and orientations of the movable elements 33 . . . 37 of the support structure 31 of the holding mechanism 9. Thus, the spatial parameters determining unit 17 is adapted to translate the determined position and orientation of the field of view 60 and hence of the ultrasound probe 8 into movable element parameters defining the positions and orientations of the movable elements 33 . . . 37 of the support structure 31, to which the holder 10 with the ultrasound probe 8 is attached, such that the ultrasound probe 8 is held in the position and orientation determined by the spatial parameters determining unit 17. In another embodiment the determined spatial parameters may be output to a user and the user may manually position and orient the ultrasound probe 8 accordingly.

After the ultrasound probe 8 has been positioned and oriented in accordance with the determined spatial parameters, an ultrasound image is generated, wherein the ultrasound image as well as the reference image 40 is registered with the radiation device 4 by using known registration techniques. The treatment plan providing unit 12 is arranged to adapt the treatment plan on the basis of a comparison of the reference image and the ultrasound image. Alternatively or in addition, a controller 18 of the system 1 can be used for controlling the patient support 3 on the basis of a comparison of the reference image and the ultrasound image. The adaptation of the treatment plan and/or the control of the patient support 3 are performed such that the optionally adapted treatment plan is in accordance with the current position, orientation and dimensions of the relevant structures within the patient, especially of the target to be treated and the organs at risk. Finally, the radiation device 4 is operated in accordance with the treatment plan.

Figure 10:
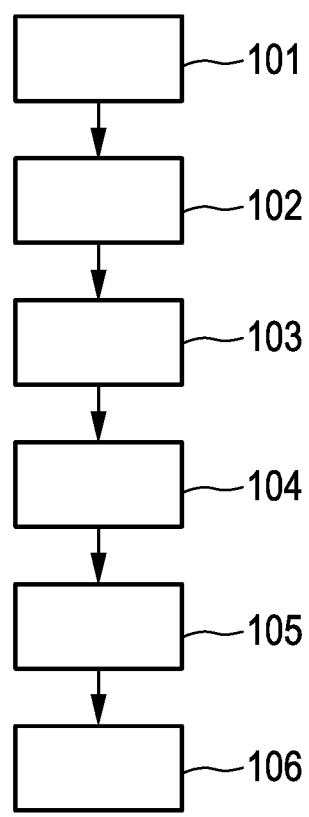
FIG. 10 shows a flowchart exemplarily illustrating an embodiment of a method for assisting in providing an image.

In the following an embodiment of a method for assisting in providing an image will exemplarily be described with reference to a flowchart shown in FIG. 10.

In step 101 a treatment plan is provided by the treatment plan providing unit 12 and the reference image providing unit 13 provides a planning image, which has been used for generating the treatment plan, as a reference image showing the target 52, organs at risk 51 and ultrasound blocking structures 50. The imaging part indication providing unit 14 provides imaging part indications defining mandatory parts of the organs at risk to be mandatorily ultrasonically imaged and optional parts of the organs at risk to be optionally ultrasonically imaged. Furthermore, the field of view providing unit 16 provides the field of view of the ultrasound probe 8.

In step 102 the spatial parameters determining unit 17 determines the spatial parameters, which define the position and orientation of the ultrasound probe 8, based on the positions, orientations and dimensions of the target 52, of the organs at risk 51 and of the ultrasound blocking structures 50 in the provided reference image, the provided field of view and the imaging part indications. In step 103 the ultrasound probe 8 is positioned and oriented in accordance with the determined spatial parameters, and in step 104 an ultrasound image of the interior of the patient 2 is generated by using the ultrasound probe 8 at the position and in the orientation defined by the spatial parameters.

In step 105 the treatment plan providing unit 12 adapts the treatment plan on the basis of a comparison of the reference image and the ultrasound image. Alternatively or in addition, the controller 18 controls the patient support 3 on the basis of a comparison of the reference image and the ultrasound image. In step 106 the radiation is applied to the patient in accordance with the treatment plan.

Radiotherapy is one of the possible treatment methods for various types of cancer. In order to deliver a high radiation dose to the tumor tissue, i.e. to the target, while sparing normal tissue, especially organs at risk, as much as possible, correct patient set up is crucial. Imaging of the treated region during the course of the treatment as it is used in image guided radiotherapy (IGRT) can contribute to a correct set up and in this way improve the accuracy of the radiation dose delivery.

An ultrasound imaging system is a relatively fast and cheap imaging modality that allows high contrast imaging of, for instance, soft tissue. In addition, it is harmless for the patient and it is presently the only volumetric imaging technique that allows real time organ tracking during a radiotherapy treatment. For these reasons an ultrasound imaging system is very suitable for image guiding purposes. However, in general ultrasound imaging requires very skilled operators, wherein training these operators requires a significant amount of time with steep learning curves. Unexpected turnovers or illness of a skilled operator can interfere with the clinical routine producing discomfort or, even more, serious damage for the patient. For this reason generally, instead of ultrasound imaging, modalities are used, which have "one button" procedures which do almost not need any training. In particular, generally cone beam computed tomography (CBCT) or portal imaging are used for interfraction monitoring.

In order to overcome these drawbacks, the system and method described above with reference to FIGS. 1 to 10 introduce a certain degree of automation into an ultrasound guidance workflow for radiotherapy. This automation can allow for user-independent ultrasound imaging and especially improve the usability for relatively untrained operators. This can results in better outcomes for the patients, while reducing toxicity and improving quality of life at the same time.

Several steps of the ultrasound guidance workflow for radiotherapy are automated. The system uses a reference image of the patient such as a computed tomography image, in order to calculate the optimal position of the ultrasound probe to achieve the best visualization of the relevant anatomical structures, i.e. of the target and the organs at risk. Spatial parameters are determined, which can be directly fed to a holding mechanism comprising a holder for holding the ultrasound probe like a robotic arm or which can be provided to an operator, in order to give detailed information how to position the ultrasound probe. Also in the latter case the ultrasound probe can be held by using a probe holder which might be designed for the respective specific body region.

In particular, prior to radiotherapy treatment commencement an initial computed tomography image can be generated, because it can provide the electron density information for radiation dose calculations. Based on this initial computed tomography image the treatment plan can be generated. Moreover, based on this computed tomography image the optimal ultrasound probe position and orientation can be calculated for each individual patient, i.e. the spatial parameters defining the optimal position and orientation of the ultrasound probe are determined. This calculation preferentially considers the presence of the relevant anatomical structures, i.e. of the target and the organs at risk, and the presence of ultrasound blocking structures like bones, which can cause shading effects and so deteriorate the quality of the ultrasound images, in the field of view of the ultrasound probe. The determination of the position of the ultrasound probe can also consider specifics of the ultrasound probe and corresponding image reconstruction techniques. Besides the field of view of the ultrasound probe, further characteristics of the ultrasound probe and/or of the reconstruction of the ultrasound image based on ultrasound signals received from the ultrasound probe can be used for determining the position and orientation of the ultrasound probe on the basis of the reference image. For instance, the size of the ultrasound probe surface, the ultrasound penetration depth, the ability to look around objects, the kind of ultrasound probe, i.e., for example, linear, phased array, et cetera can be considered.

The ultrasound probe can be placed in a probe holder that might be designed specifically for the respective body region. For instance, an ultrasound probe for transperineal scanning can be adapted to provide four degrees of freedom, i.e. four parameters might be varied for modifying its position. The maximum clockwise rotation around the y axis, i.e. around a longitudinal axis of the ultrasound probe, might in this case be, for instance, three degrees. An ultrasound probe for transabdominal scanning might also have, for example, four degrees of freedom around the y direction. In this case the maximum clockwise rotation around the x axis might be larger than three degrees.

The probe holder can be attached to a mechanical arm, a robotic arm or another device that enables the spatial positioning, i.e. to a support structure having movable elements. The user, i.e. the operator, can then be provided with information how to set the probe holder in such a way that, in the end, the real probe position and orientation matches the calculated optimal probe position and orientation for the specific patient. For example, in case of a mechanical arm each joint connecting two movable elements of the mechanical arm could contain encoders, wherein the user may be provided with information how to set each individual encoder, wherein this information is provided by the spatial parameters. Thus, the spatial parameters can provide information how to set the individual encoders.

After the ultrasound probe has been positioned in accordance with the determined spatial parameters, one or several ultrasound images are acquired. Artificial intelligence techniques can be applied on the acquired ultrasound images, in order to allow for an automatic interpretation of the ultrasound images and, in case necessary, adaption. In particular, changes in the internal tissue distribution of the patient can lead to differences between the expected ultrasound image, i.e. the ultrasound image expected from the determination of the position and orientation of the field of view of the ultrasound probe relative to the target, the organs at risk and the ultrasound blocking structures, and the actually acquired ultrasound image. The system, especially the spatial parameters determination system and/or the ultrasound imaging system, can be adapted to use artificial intelligence for automatically interpreting the actually acquired ultrasound image. In particular, the system can be adapted to access the actually acquired ultrasound images with respect to, for instance, a) the visibility of the relevant anatomical structures, i.e. the target, the organs at risk and the ultrasound blocking structures, in the actually acquired ultrasound image, b) an occurrence of unexpected shading that deteriorates the quality of the actually acquired ultrasound image, c) a presence of air bubbles or other phenomena in the actually acquired ultrasound images indicating a poor coupling between the ultrasound probe and the skin of the patient, and d) a presence of a sufficient spatially variable resolution for each of the scanned elements. Preferentially, the respective assessment results are compared with predetermined standards and it is determined whether the assessment results differ by more than a respective predefined threshold from these standards. If this is the case, the differences can be reduced preferentially without moving the ultrasound probe.

The system and method described above with reference to FIGS. 1 to 10 can be used for providing an operator with information on how to position and orient an ultrasound probe for four-dimensional transperineal ultrasound image acquisition for verifying prostate cancer radiotherapy. This information on how to position and orient the ultrasound probe is provided based on a reference image being preferentially a computed tomography image which has also been used for generating a treatment plan.

The holding mechanism for holding the ultrasound probe can be arranged to receive the determined spatial parameters defining the position and orientation of the ultrasound probe from the spatial parameters determining unit. However, alternatively or in addition, the holding mechanism can comprise a user interface for entering the determined position and orientation of the ultrasound probe, wherein the holding mechanism can be arranged to assume a corresponding position and orientation.

Although in the above described embodiments the energy source is a radiation source for applying energy to the target by using radiation emitted by the radiation source, in other embodiments other energy sources, i.e. other treatment delivery means, can be used for applying the energy. For instance, the energy source can be adapted to deliver thermal energy, in particular by means of a needle, or high intensity focused ultrasound (HIFU) energy.

Although it is mentioned above that the system might be used for treating prostate cancer, the system can also be adapted to treat other parts of a patient like the abdomen, especially the liver, the breast, et cetera. In particular, the system may be used for gynecological cancer cases.

Although in an above described embodiment the reference image and the ultrasound image, which has been acquired, while the ultrasound probe was arranged in the determined position and orientation, are compared, wherein, for instance, the treatment plan is modified or the positioning of the patient is modified based on the comparison, in another embodiment this ultrasound image may be compared with a further ultrasound image, which has been acquired immediately before or immediately after the reference image has been acquired, and this comparison might be used for, for example, modifying the treatment plan or the positioning of the patient.

Since the system for image based guidance for treatment delivery to a patient determines the spatial parameters defining the position and orientation of the ultrasound probe, wherein then these spatial parameters are applied for arranging the ultrasound probe accordingly and generating an ultrasound image of the patient to be used for guiding the treatment delivery, the system can also be regarded as being a system for assisting in providing, particularly generating, an image, i.e. the ultrasound image.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the provision of a treatment plan, the determination of spatial parameters defining a position and orientation of an ultrasound probe, the provision of a field of view of the ultrasound probe, the provision of imaging part indications, et cetera performed by one or several units or devices can be performed by any other number of units or devices. These operations and/or the control of the system for image based guidance of treatment delivery to a patient in accordance with the method for assisting in providing an image can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for image based guidance of treatment delivery to a patient. The system is adapted to determine spatial parameters defining a position and orientation of an ultrasound probe on the basis of a reference image which has been used for preparing a treatment plan. This can provide a certain degree of automation in arranging the ultrasound probe, in order to decrease user dependence and improve the usability for relatively untrained operators. Moreover, since the reference image is also used for generating the treatment plan, i.e. since the same image is used for generating the treatment plan and for determining the position and orientation of the ultrasound probe, it is not necessarily required to acquire an additional image. This can allow for a reduced radiation dose applied to the parts of the patient not being the target to be treated.

The invention claimed is:

1. A system for image based guidance of treatment delivery to a patient, the system comprising:
   a reference image providing unit for providing a reference image of a patient, wherein the reference image shows a target to be treated and an organ at risk within the patient;
   a treatment plan providing unit for providing a treatment plan for the treatment delivery, which plan has been prepared on the basis of the reference image;
   a spatial parameters determining unit for determining spatial parameters defining a position and orientation of an ultrasound probe coupled to the system, the ultrasound probe adapted to be used for generating an ultrasound image of the patient, on the basis of the reference image; and
   an imaging part indication providing unit for providing an imaging part indication defining a mandatory part of the organ at risk to be mandatorily ultrasonically imaged and an optional part of the organ at risk to be optionally ultrasonically imaged;

wherein the system further comprises a field of view providing unit for providing a field of view of the ultrasound probe and wherein the spatial parameters determining unit is adapted to determine a position, an orientation and dimensions of the target within the reference image, to determine a position, an orientation and dimensions of the organ at risk within the reference image, and to determine the spatial parameters based on the determined positions, orientations and dimensions of the target and the organ at risk in the reference image, the provided imaging part indication, and the provided field of view such that the target and the organ at risk are within the field of view.

2. The system of claim 1, wherein the reference image also shows an ultrasound blocking structure, wherein the spatial parameters determining unit is adapted to also determine a position, an orientation and dimensions of the ultrasound blocking structure within the reference image, wherein the spatial parameters determining unit is adapted to determine the spatial parameters also based on the determined position, orientation and dimensions of the ultrasound blocking structure.

3. The system of claim 2, wherein the spatial parameters determining unit is adapted to determine, without considering the position, orientation and dimensions of the ultrasound blocking structure, several sets of spatial parameters defining several possible positions and orientations of the ultrasound probe such that in each position and orientation at least the target is within the provided field of view and to select, by considering the position of the ultrasound blocking structure, at least one of these sets of spatial parameters which defines a possible position and orientation, at which the ultrasound blocking structure is not in between the ultrasound probe and at least the target to be ultrasonically imaged.

4. The system of claim 1, wherein the system further comprises a holding mechanism for holding the ultrasound probe in accordance with the determined spatial parameters such that the ultrasound probe assumes the position and orientation defined by the determined spatial parameters.

5. The system of claim 4, wherein the holding mechanism comprises a holder for holding the ultrasound probe and a support structure to which the holder is attached, wherein the position and orientation of the support structure is modifiable by modifying positions and/or orientations of movable elements of the support structure, which are defined by movable element parameters, wherein the spatial parameters determining unit is adapted to determine, as the spatial parameters defining the position and orientation of the ultrasound probe, the movable element parameters.

6. The system of claim 1, wherein the system further comprises an ultrasound image providing unit for providing an ultrasound image generated by using the ultrasound probe in the position and orientation defined by the determined spatial parameters, wherein the treatment plan providing unit is arranged to adapt the treatment plan on the basis of a comparison of the reference image and the ultrasound image.

7. The system of claim 1, wherein the system further comprises an ultrasound image providing unit for providing an ultrasound image generated by using the ultrasound probe in the position and orientation defined by the determined spatial parameters, wherein the system further comprises a patient support, wherein the system comprises a controller for controlling the patient support on the basis of a comparison of the reference image and the ultrasound image.

8. The system of claim 1, wherein the system further comprises an energy source for providing energy to be applied to the target in accordance with the treatment plan.

9. A method for assisting in providing an image, the method comprising:
providing a reference image of a patient, wherein the reference image shows a target to be treated and an organ at risk within the patient;
providing a treatment plan for the treatment delivery, which plan has been prepared on the basis of the reference image;
determining spatial parameters defining a position and orientation of an ultrasound probe, which is adapted to be used for generating an ultrasound image, on the basis of the reference image; and
providing an imaging part indication defining a mandatory part of the organ at risk to be mandatorily ultrasonically imaged and an optional part of the organ at risk to be optionally ultrasonically imaged;
wherein a field of view of the ultrasound probe is provided, wherein a position, an orientation and dimensions of the target within the reference image are determined, wherein a position, an orientation and dimensions of the organ at risk within the reference image are determined, and wherein the spatial parameters are determined based on the determined positions, orientations and dimensions of the target and the organ at risk in the reference image, the provided imaging part indication, and the provided field of view such that the target and the organ at risk are within the field of view.

10. A non-transitory computer readable medium comprising program code for image based guidance of treatment delivery to a patient, the program code, when executed by a controller, causing the controller to carry out the following steps:
providing a reference image of a patient, wherein the reference image shows a target to be treated and an organ at risk within the patient;
providing a treatment plan for the treatment delivery, which plan has been prepared on the basis of the reference image;
determining spatial parameters defining a position and orientation of an ultrasound probe, which is adapted to be used for generating an ultrasound image, on the basis of the reference image; and
providing an imaging part indication defining a mandatory part of the organ at risk to be mandatorily ultrasonically imaged and an optional part of the organ at risk to be optionally ultrasonically imaged;
wherein a field of view of the ultrasound probe is provided, wherein a position, an orientation and dimensions of the target within the reference image are determined, wherein a position, an orientation and dimensions of the organ at risk within the reference image are determined, and wherein the spatial parameters are determined based on the determined positions, orientations and dimensions of the target and the organ at risk in the reference image, the provided imaging part indication, and the provided field of view such that the target and the organ at risk are within the field of view.

* * * * *